(12) United States Patent
Choubey (10) Patent No.: US 11,007,073 B2
(45) Date of Patent: *May 18, 2021

(54) THIN FILM MESH HYBRID FOR TREATING VASCULAR DEFECTS

(71) Applicant: Covidien LP, Mansfield, MA (US)

(72) Inventor: Animesh Choubey, Chino, CA (US)

(73) Assignee: COVIDIEN LP, Mansfield, MA (US)

( * ) Notice: Subject to any disclaimer, the term of this patent is extended or adjusted under 35 U.S.C. 154(b) by 69 days.

This patent is subject to a terminal disclaimer.

(21) Appl. No.: 16/413,527

(22) Filed: May 15, 2019

(65) Prior Publication Data

US 2019/0269534 A1 Sep. 5, 2019

Related U.S. Application Data

(63) Continuation of application No. 15/673,596, filed on Aug. 10, 2017, now Pat. No. 10,342,686.

(51) Int. Cl.
*A61F 2/915* (2013.01)
*A61F 2/89* (2013.01)
(Continued)

(52) U.S. Cl.
CPC ............. *A61F 2/89* (2013.01); *A61F 2/88* (2013.01); *A61F 2/915* (2013.01); *A61F 2002/823* (2013.01); *A61F 2002/825* (2013.01); *A61F 2002/91558* (2013.01); *A61F 2002/91583* (2013.01); *A61F 2210/0014* (2013.01); *A61F 2230/0091* (2013.01); *A61F 2240/001* (2013.01); *A61F 2250/0037* (2013.01); *A61F 2250/0098* (2013.01)

(58) Field of Classification Search
CPC ............. A61F 2/915; A61F 2002/9155; A61F 2250/0036; A61F 2250/0037
See application file for complete search history.

(56) References Cited

U.S. PATENT DOCUMENTS 8,603,014 B2 12/2013 Alleman et al.
8,837,800 B1 9/2014 Bammer et al.
(Continued)

FOREIGN PATENT DOCUMENTS

EP 2319575 B1 11/2013
GB 2494820 A 3/2013
(Continued)

OTHER PUBLICATIONS

Extended European Search Report dated Mar. 29, 2021; European Application No. 18844209.9; 8 pages.

*Primary Examiner* — Suba Ganesan
(74) *Attorney, Agent, or Firm* — Fortem IP LLP; Mary Fox (57) ABSTRACT

Devices that can be delivered into a vascular system to divert flow are disclosed herein. According to some embodiments, devices are provided for treating aneurysms b diverting flow. An expandable device can comprise, for example, a plurality of strut regions and a plurality of bridge regions. Each of the strut regions may extend circumferentially about the expandable device and include a plurality of struts. Each of the plurality of bridge regions may be attached to and extend between two of the strut regions and comprise a plurality first bridges and second bridges that intersect one another and are movable relative to one another at their intersections.

27 Claims, 5 Drawing Sheets

(51) Int. Cl.
*A61F 2/88* (2006.01)
*A61F 2/82* (2013.01)

(56) References Cited

U.S. PATENT DOCUMENTS

| | | |
|---|---|---|
| 8,915,950 B2 | 12/2014 | Cam et al. |
| 8,940,003 B2 | 1/2015 | Slee et al. |
| 9,119,656 B2 | 9/2015 | Bose et al. |
| 9,126,018 B1 | 9/2015 | Garrison |
| 9,180,031 B2 | 11/2015 | Vogel et al. |
| 9,211,132 B2 | 12/2015 | Bowman |
| 9,241,699 B1 | 1/2016 | Kume et al. |
| 9,265,512 B2 | 2/2016 | Garrison et al. |
| 9,308,007 B2 | 4/2016 | Cully et al. |
| 9,399,118 B2 | 7/2016 | Kume et al. |
| 9,445,828 B2 | 9/2016 | Turjman et al. |
| 9,445,829 B2 | 9/2016 | Brady et al. |
| 9,492,637 B2 | 11/2016 | Garrison et al. |
| 9,539,022 B2 | 1/2017 | Bowman |
| 9,561,345 B2 | 2/2017 | Garrison et al. |
| 9,579,119 B2 | 2/2017 | Cully et al. |
| 9,585,741 B2 | 3/2017 | Ma |
| 9,603,732 B2 | 3/2017 | Ma et al. |
| 9,642,635 B2 | 5/2017 | Vale et al. |
| 9,655,633 B2 | 5/2017 | Leynov et al. |
| 9,737,318 B2 | 8/2017 | Monstadt et al. |
| 9,770,251 B2 | 9/2017 | Bowman et al. |
| 9,801,643 B2 | 10/2017 | Hansen et al. |
| 9,861,783 B2 | 1/2018 | Garrison et al. |
| 9,993,257 B2 | 6/2018 | Losordo et al. |
| 10,028,782 B2 | 7/2018 | Orion |
| 10,029,008 B2 | 7/2018 | Creighton |
| 10,039,906 B2 | 8/2018 | Kume et al. |
| 2005/0209678 A1 | 9/2005 | Henkes et al. |
| 2010/0010622 A1* | 1/2010 | Lowe .............. A61F 2/91 623/1.16 |
| 2010/0023105 A1 | 1/2010 | Levy et al. |
| 2010/0268326 A1 | 10/2010 | Leynov et al. |
| 2011/0184452 A1 | 7/2011 | Huynh et al. |
| 2011/0184453 A1 | 7/2011 | Levy et al. |
| 2013/0030461 A1 | 1/2013 | Marks et al. |
| 2013/0281788 A1 | 10/2013 | Garrison |
| 2014/0107764 A1 | 4/2014 | Bressloff et al. |
| 2014/0249616 A1 | 9/2014 | Strauss et al. |
| 2014/0276074 A1 | 9/2014 | Warner |
| 2014/0343595 A1 | 11/2014 | Monstadt et al. |
| 2015/0359547 A1 | 12/2015 | Vale et al. |
| 2016/0015402 A1 | 1/2016 | Brady et al. |
| 2016/0015935 A1 | 1/2016 | Chan et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113665 A1 | 4/2016 | Brady et al. |
| 2016/0151618 A1 | 6/2016 | Powers et al. |
| 2016/0157985 A1 | 6/2016 | Vo et al. |
| 2016/0199620 A1 | 7/2016 | Pokorney et al. |
| 2016/0296690 A1 | 10/2016 | Kume et al. |
| 2016/0302808 A1 | 10/2016 | Loganathan et al. |
| 2016/0317331 A1 | 11/2016 | Sano et al. |
| 2016/0375180 A1 | 12/2016 | Anzai |
| 2017/0079766 A1 | 3/2017 | Wang et al. |
| 2017/0079767 A1 | 3/2017 | Leon-Yip |
| 2017/0086862 A1 | 3/2017 | Vale et al. |
| 2017/0100143 A1 | 4/2017 | Grandfield |
| 2017/0105743 A1 | 4/2017 | Vale et al. |
| 2017/0164963 A1 | 6/2017 | Goyal |
| 2017/0215902 A1 | 8/2017 | Leynov et al. |
| 2017/0224953 A1 | 8/2017 | Tran et al. |
| 2017/0281909 A1 | 10/2017 | Northrop et al. |
| 2017/0290599 A1 | 10/2017 | Youn et al. |
| 2018/0049762 A1 | 2/2018 | Seip et al. |
| 2018/0084982 A1 | 3/2018 | Yamashita et al. |
| 2018/0116717 A1 | 5/2018 | Taff et al. |
| 2018/0132876 A1 | 5/2018 | Zaidat |
| 2018/0140314 A1 | 5/2018 | Goyal et al. |
| 2018/0140315 A1 | 5/2018 | Bowman et al. |
| 2018/0140354 A1 | 5/2018 | Lam et al. |
| 2018/0185614 A1 | 7/2018 | Garrison et al. |

FOREIGN PATENT DOCUMENTS

| | | |
|---|---|---|
| JP | 2004016668 A | 1/2004 |
| JP | 2005532887 A | 11/2005 |
| JP | 2006026423 A | 2/2006 |
| JP | 2006095095 A | 4/2006 |
| JP | 2014004219 A | 1/2014 |
| JP | 2018118132 A | 8/2018 |
| KR | 20180102877 A | 9/2018 |
| WO | 2015141317 A1 | 9/2015 |
| WO | 2017192999 A1 | 11/2017 |
| WO | 2018019829 A1 | 2/2018 |
| WO | 2018033401 A1 | 2/2018 |
| WO | 2018046408 A2 | 3/2018 |
| WO | 2018137029 A1 | 8/2018 |
| WO | 2018137030 A1 | 8/2018 |
| WO | 2018145212 A1 | 8/2018 |
| WO | 2018156813 A1 | 8/2018 |
| WO | 2018172891 A1 | 9/2018 |
| WO | 2018187776 A1 | 10/2018 |

* cited by examiner

THIN FILM MESH HYBRID FOR TREATING VASCULAR DEFECTS

CROSS REFERENCE TO RELATED APPLICATIONS

The present application is a continuation application of U.S. application Ser. No. 15/673,596, filed Aug. 10, 2017, which is incorporated herein by reference in its entirety.

TECHNICAL FIELD

The present technology relates generally to methods and devices for treating vascular defects, and particularly to diverting blood flow from a blood vessel into an aneurysm. Some embodiments of the present technology relate to flow-diverting mesh devices.

BACKGROUND

Aneurysms are an abnormal bulging or ballooning of a blood vessel that can result from the vessel wall being weakened by disease, injury, or a congenital abnormality. Aneurysms have thin, weak walls and have a tendency to rupture, which can lead to stroke, death, disability, etc. One method of treating aneurysms includes inserting a flow-diverting stent or braid into a parent vessel that includes the aneurysm to be treated. Such stents or braids can be inserted into a vessel in a collapsed state, positioned next to the neck of the aneurysm, and expanded into apposition with the vessel wall. If the stent or braid has a sufficiently low porosity, it can function to block the flow of blood through the device and into the aneurysm to induce embolization of the aneurysm.

However, some aneurysms—and especially cerebral aneurysms—are located in small and tortuous portions of the vasculature. Current designs for flow-diverting stents or braids have difficulty achieving a snug fit across the neck of the aneurysm if the parent vessel is curved, twisted, or forked. For example, current designs generally suffer from crimping or kinking when positioned in such tortuous vessels. This can make it more difficult to position a flow-diverting device and can cause the device to have an inadequate porosity as the device is expanded within the vessel. Also, current designs often undesirably block blood flow to branching or secondary vessels that are close to the aneurysm. Accordingly, there exists a need for improved flow-diverting devices for treating aneurysms.

SUMMARY

Expandable devices can be delivered into vascular system to divert flow. According to some embodiments, expandable devices are provided for treating aneurysms by diverting flow. A flow-diverting expandable device can comprise a plurality of struts and/or bridges and be configured to be implanted in a blood vessel. The expandable device can be expandable to an expanded state at an aneurysm. The expandable device can have at least a section for spanning the neck of the aneurysm and a plurality of pores or openings located between the struts/bridges. The expandable device can have a sidewall and a plurality of pores/openings in the sidewall that are sized to inhibit flow of blood through the sidewall into an aneurysm to a degree sufficient to lead to thrombosis and healing of the aneurysm when the expandable device is positioned in a blood vessel and adjacent to the aneurysm. The subject technology is illustrated, for example, according to various aspects described below.

Further, some embodiments can provide a delivery system for treating an aneurysm. The system can comprise a microcatheter configured to be implanted into a blood vessel, a core member, extending within the microcatheter, having a distal segment, and the device extending along the core member distal segment.

The subject technology is illustrated, for example, according to various aspects described below. Various examples of aspects of the subject technology are described as numbered clauses (1, 2, 3, etc.) for convenience. These are provided as examples and do not limit the subject technology.

Clause 1. An expandable device comprising:
  a plurality of strut regions extending circumferentially about the expandable device and including a plurality of struts; and
  a plurality of bridge regions extending between adjacent strut regions and including a plurality of bridges, the plurality of bridges including first bridges and second bridges, wherein each of the first bridges intersects one or more of the second bridges within each of the bridge regions, and wherein the first bridge is configured to move relative to the second bridge at each of the intersections.

Clause 2. The expandable device of Clause 1, wherein the first bridges extend in a first rotational direction and the second bridges extend in a second rotational direction different than the first rotational direction.

Clause 3. The expandable device of Clause 1 or Clause 2, wherein each of the struts is coupled to another strut at an apex.

Clause 4. The expandable device of Clause 3, wherein at least some of the apices connect to one of (a) one of the first bridges or (b) one of the second bridges.

Clause 5. The expandable device of Clause 3 or Clause 4, wherein at least one of the apices connects to one of the first bridges and to one of the second bridges.

Clause 6. The expandable device of any one of Clauses 3-5, wherein the first bridges connect to the apices at a first elevation and the second bridges connect to the apices at a second elevation different than the first elevation.

Clause 7. The expandable device of any one of Clauses 3-6, wherein at least some of the apices are free apices such that they are not connected to one of the bridges.

Clause 8. The expandable device of any one of Clauses 1-7, wherein the struts may be connected end-to-end within the strut regions such that the struts are circumferentially disposed in a zig-zag pattern.

Clause 9. The expandable device of any one of Clauses 1-8, wherein the lengths of each of the strut regions measured along the longitudinal axis of the device remain constant when the device is elongated or compressed along its longitudinal axis.

Clause 10. The expandable device of any one of Clauses 1-9, wherein the lengths of the bridge regions measured along the longitudinal axis of the device change when the device is elongated or compressed along its longitudinal axis.

Clause 11. The expandable device of any one of Clauses 1-10, wherein the first bridge is spaced apart from the one or more second bridges at each intersection.

Clause 12. The expandable device of any one of Clauses 1-11, wherein the first bridge contacts the one or more second bridges at each intersection.

Clause 13. The expandable device of any one of Clauses 1-12, wherein the expandable device is formed by thin-film deposition.

Clause 14. The expandable device of any one of Clause 1-13, wherein the expandable device is made of one or more superelastic materials.

Clause 15. The expandable device of any one of Clause 1-14, wherein the expandable device is non-braided.

Clause 16. The expandable device of any one of Clauses 1-15, wherein the struts have a strut thickness and each strut has a strut edge surface extending along the strut thickness, and the bridges connect to and extend from the strut edge surfaces.

Clause 17. The expandable device of Clause 16, wherein the first bridges have a first bridge thickness less than the strut thickness.

Clause 18. The expandable device of Clause 17, wherein the second bridges have a second bridge thickness less than the strut thickness.

Clause 19. The expandable device of Clause 18, wherein the combined first and second bridge thicknesses are less than or equal to the strut thickness.

Clause 20. The expandable device of any one of Clauses 16-19, wherein the strut thickness is measured along a line orthogonal to and extending radially from a central longitudinal axis of the expandable device.

Clause 21. The expandable device of any one of Clauses 16-20, wherein the bridges connect to and extend from the struts at apices formed by the struts.

Clause 22. An expandable device comprising:
a plurality of strut regions extending circumferentially about the expandable device and including a plurality of struts arranged end-to-end; and
a plurality of bridge regions extending between adjacent strut regions and including a plurality of bridges, the plurality of bridges including first bridges and second bridges that intersect one another within the bridge regions and together define a plurality of cells, wherein each of the cells enclose a cell area, and wherein the bridge regions are configured such that the cell areas decrease or increase in response to elongation or compression, respectively, of the expandable device along its longitudinal axis.

Clause 23. The expandable device of Clause 22, wherein the first bridges extend in a first rotational direction and the second bridges extend in a second rotational direction different than the first rotational direction.

Clause 24. The expandable device of Clause 22 or Clause 23, wherein each of the struts is coupled to another strut at an apex.

Clause 25. The expandable device of Clause 24, wherein at least some of the apices connect to one of (a) one of the first bridges or (b) one of the second bridges.

Clause 26. The expandable device of Clause 24 or Clause 25, wherein at least one of the apices connects to one of the first bridges and to one of the second bridges.

Clause 27. The expandable device of any one of Clauses 24-26, wherein the first bridges connect to the apices at a first elevation and the second bridges connect to the apices at a second elevation different than the first elevation.

Clause 28. The expandable device of any one of Clauses 22-27, wherein the expandable device is formed by thin-film deposition.

Clause 29. The expandable device of any one of Clauses 22-28, wherein the expandable device is made of one or more superelastic materials.

Clause 30. The expandable device of any one of Clauses 22-29, wherein the first bridges are moveable relative to the second bridges at the intersections.

Clause 31. The expandable device of any one of Clauses 22-30, wherein the expandable device is non-braided.

Clause 32. The expandable device of any one of Clauses 22-31, wherein the struts have a strut thickness and each strut has a strut edge surface extending along the strut thickness, and the bridges connect to and extend from the strut edge surfaces.

Clause 33. The expandable device of Clause 32, wherein the first bridges have a first bridge thickness less than the strut thickness.

Clause 34. The expandable device of Clause 33, wherein the second bridges have a second bridge thickness less than the strut thickness.

Clause 35. The expandable device of Clause 34, wherein the combined first and second bridge thicknesses are less than or equal to the strut thickness.

Clause 36. The expandable device of any one of Clauses 32-35, wherein the strut thickness is measured along a line orthogonal to and extending radially from a central longitudinal axis of the expandable device.

Clause 37. The expandable device of any one of Clauses 32-36, wherein the bridges connect to and extend from the struts at apices formed by the struts.

Clause 38. An expandable device comprising:
a plurality of strut regions extending circumferentially about the expandable device and including a plurality of struts; and
a plurality of bridge regions extending between adjacent strut regions and including a plurality of bridges, the plurality of bridges including first bridges and second bridges, wherein each of the first bridges is positioned radially inwardly each of the second bridges along their respective lengths.

Clause 39. The expandable device of Clause 38, wherein the expandable device is formed by thin-film deposition.

Clause 40. The expandable device of Clause 38 or Clause 39, wherein the second bridges cross over the first bridges at intersections within the bridge regions, and wherein the first bridges are free to move relative to the second bridges at the intersections.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

DETAILED DESCRIPTION

In the following detailed description, specific details are set forth to provide an understanding of the present technology. However, the present technology may be practiced without some of these specific details. In some instances, well-known structures and techniques have not been shown in detail so as not to obscure the present technology.

The terminology used in the description presented below is intended to be interpreted in its broadest reasonable manner, even though it is being used in conjunction with a detailed description of certain specific embodiments of the disclosure. Certain terms may even be emphasized below; however, any terminology intended to be interpreted in any restricted manner will be overtly and specifically defined as such in this Detailed Description section.

Aspects of the present disclosure are directed generally toward devices that can be delivered into a vascular system to divert flow. According to some embodiments, such devices are provided for treating aneurysms by diverting flow. For example, a device according to the present technology can be configured to interfere with blood flow to generally reduce the exchange of blood between a parent vessel and an aneurysm, which can induce thrombosis of the aneurysm. A device (or a device component, such as a frame and/or mesh) that interferes with blood flow can be said to have a "flow diverting" property.

Figure 1A:
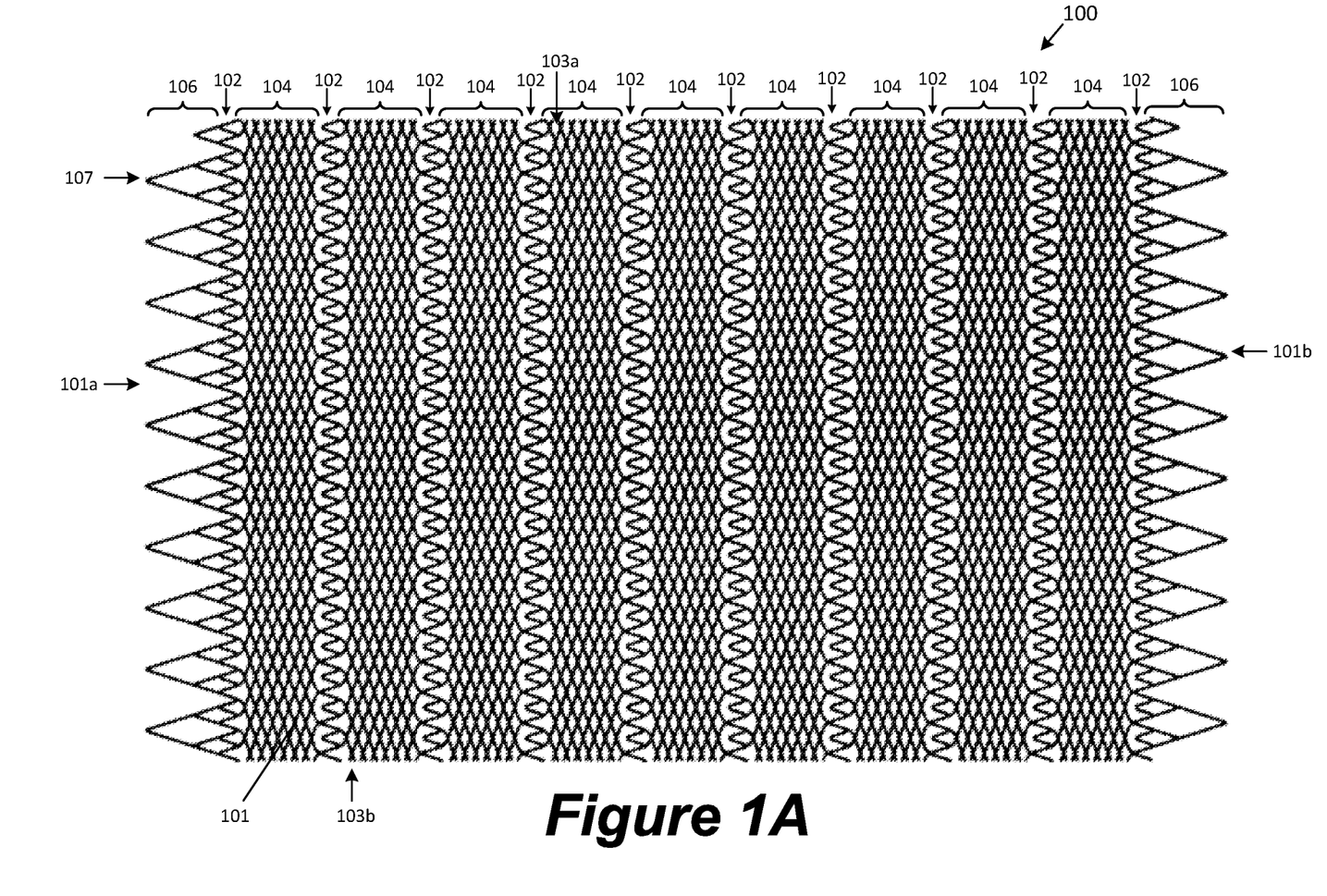
FIG. 1A is a plan view of a flow-diverting device configured in accordance with the present technology.
Figure 1B:
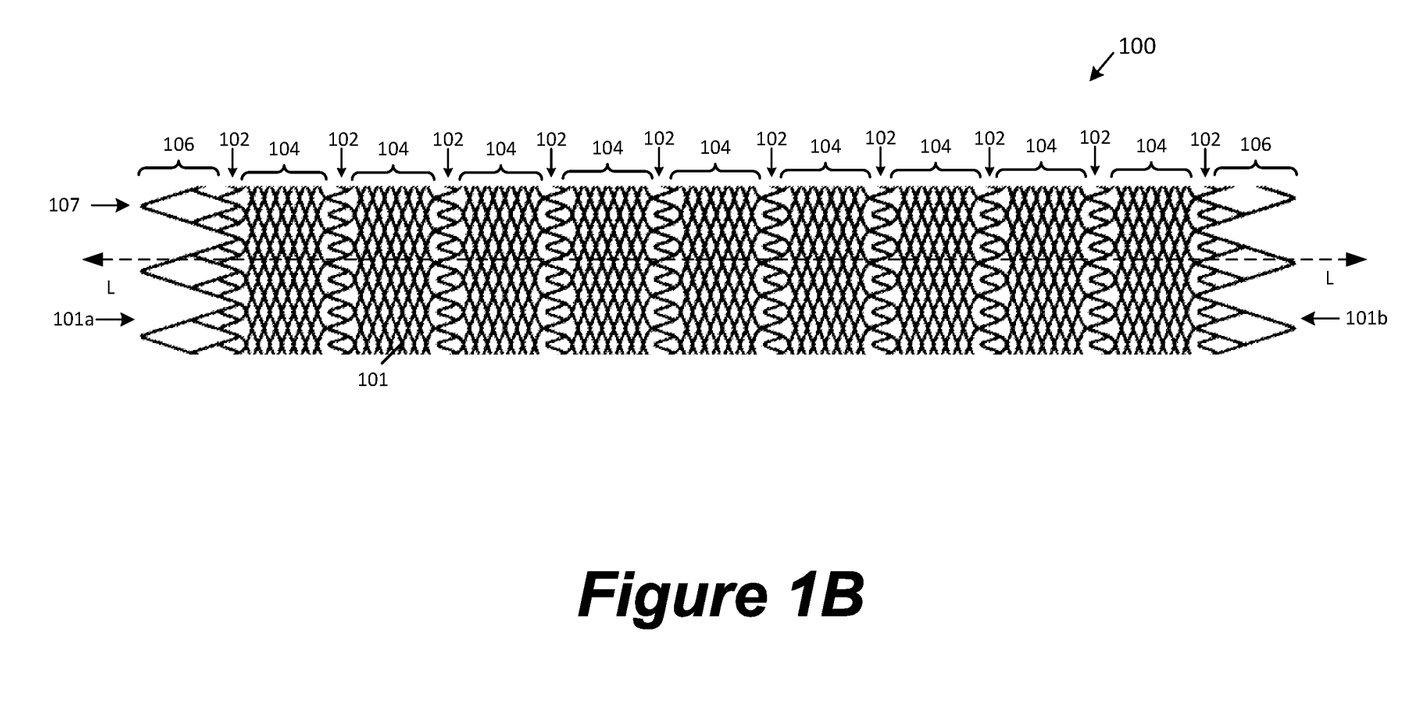
FIG. 1B is a schematic illustration of the device shown in FIG. 1A, showing the device in a tubular configuration.

FIG. 1A is a plan view of an expandable device 100 (or "device 100") in an uncurled or laid-flat configuration. As shown in FIG. 1A, the device 100 includes a mesh 101 having a proximal end 101a, a distal end 101b, and longitudinal edges 103a, 103b extending between the proximal and distal ends 101a, 101b. FIG. 1B is a side view of the device 100 of FIG. 1A showing the mesh 101 in a tubular configuration in which the mesh 101 is curled up from the laid-flat configuration such that longitudinal edges 103a and 103b (not shown in FIG. 1B) are positioned adjacent to or in contact with one another. In the tubular configuration, the mesh 101 surrounds a lumen extending between open ends of the device 100. In some embodiments, the longitudinal edges 103a and 103b may overlap when the device 100 is in the tubular configuration, or the device 100 can be configured as a continuous tube (without overlapping edges) wherein the mesh is circumferentially continuous about the longitudinal axis of the device 100 and the edges 103a, 103b don't exist except as useful reference points in a "laid-flat" depiction such as in FIG. 1A. As used herein, the term "longitudinal" can refer to a direction along an axis that extends through the lumen of the device while in a tubular configuration, and the term "circumferential" can refer to a direction along an axis that is orthogonal to the longitudinal axis and extends around the circumference of the device when in a tubular configuration.

Figure 2A:
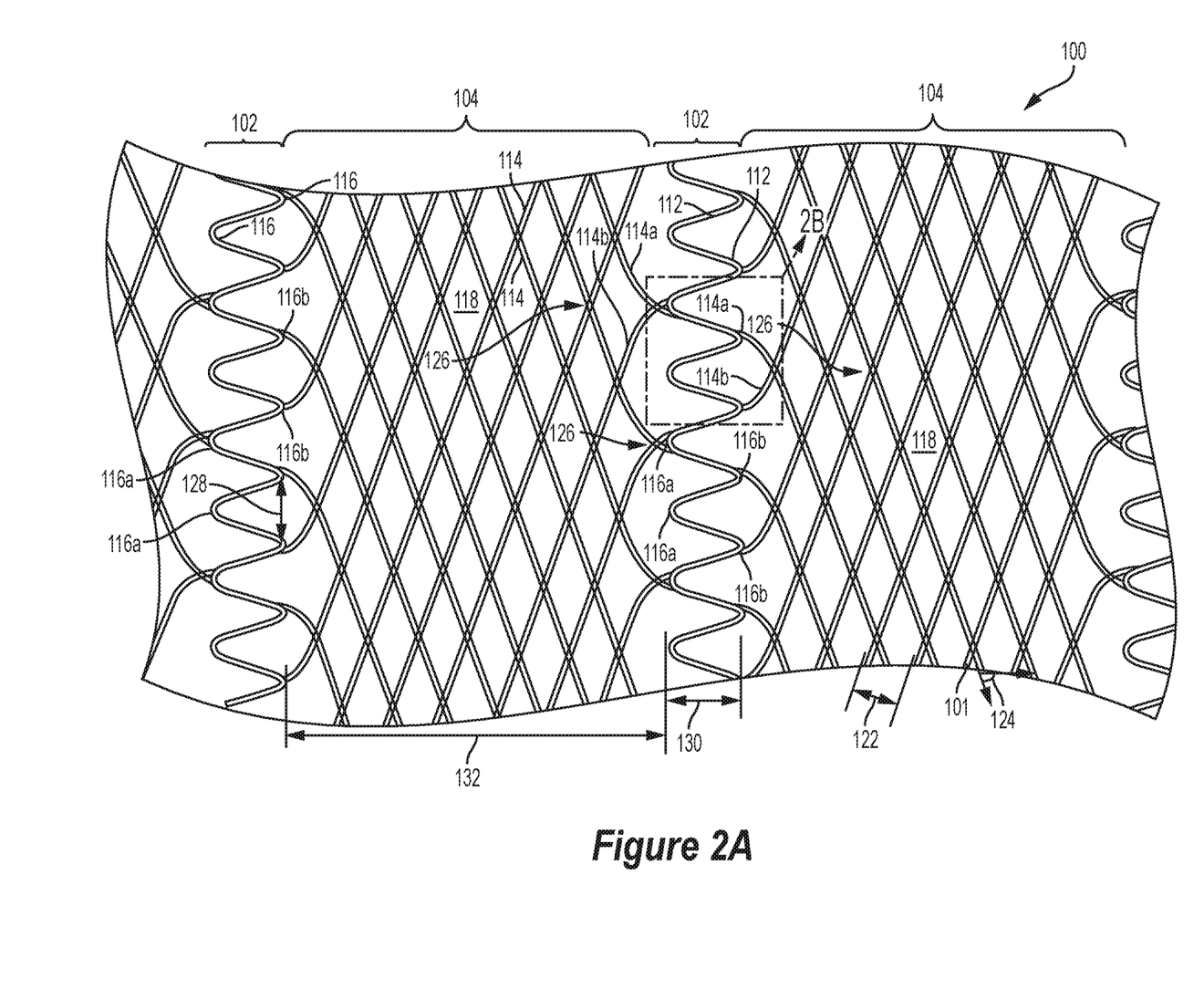
FIG. 2A is an enlarged view of a portion of the device as shown in FIG. 1A.

FIG. 2A is an enlarged view of a portion of the mesh 101 as shown in FIG. 1A. Referring to FIGS. 1A-2A, the mesh 101 may include a plurality of strut regions 102 and a plurality of bridge regions 104, each of which extend circumferentially around the mesh 101 when the mesh 101 is in the tubular configuration. In some embodiments, the mesh 101 further includes optional tapered regions 106 at its proximal and distal ends 101a, 101b. The plurality of strut regions 102 may include a plurality of struts 112, and the plurality of bridge regions 104 may include a plurality of bridges 114 that extend longitudinally between adjacent strut regions 102. Within some or all of the strut regions 102, the struts 112 may be connected end-to-end to form alternating "V's" such that the struts 112 are circumferentially disposed in a zig-zag or "Z" pattern. Adjacent struts 112 may connect to one another at apices 116, and the strut regions 102 may have first apices 116a that point towards the proximal end 101a of the mesh 101 and second apices 116b that point towards the distal end 101b of the mesh 101. Some or all of the apices 116 can be formed at longitudinal ends of the strut region 102, such that each of the apices 116 faces an adjoining bridge region 104. Each strut region 102 can have, e.g., 28-108 struts 112.

According to some embodiments, for example as shown in FIGS. 1A and 1B, the bridges 114 of the bridge regions 104 can be connected to the struts 112 of adjacent strut regions 102. For example, in some embodiments each of the bridges 114 can connect to a strut 112 at a first apex 116a of one strut region 102 with one end of the bridge 114, and the opposite end of the bridge 114 may connect to a strut 112 at a second apex 116b of another strut region 102. In some embodiments, one or both of the ends of one or more bridges 114 is connected at a midpoint (or elsewhere along the length) of a strut 112 (e.g., not at an apex 116). Between the ends of the bridge 114, the bridge 114 can be non-branching. Between the ends of the bridge 114, the bridge 114 can be unconnected to any other bridge 114. Each bridge region 104 can have, e.g., 28-108 bridges 114. Each bridge 114 can span a circumferential distance of the expandable device 100 while the expandable device 100 is in a tubular shape. For example, each bridge 114 can span 30 degrees to 180 degrees about the longitudinal axis, for example 120 degrees. By further example, each bridge 114 can span a distance of 3 to 54 apices 116 between terminal ends of the bridge 114.

In some embodiments, the bridges 114 may include first bridges 114a and second bridges 114b. According to some embodiments, within some or all of the bridge regions 104 having first and second bridges 114a and 114b, the first bridges 114a may extend in a first rotational direction (e.g., clockwise) with respect to the longitudinal axis L (FIG. 1B) of the device 100 and the second bridges 114b may extend in a second rotational direction opposite the first rotational direction (e.g., counterclockwise) with respect to the longitudinal axis L. As such, a first bridge 114a may intersect multiple second bridges 114b along its length (or vice versa), thus forming a plurality of intersections 126 at which the first and second bridges 114a, 114b cross one another. As a result, some or all of the bridge regions 104 may include a plurality of cells 118 having sidewalls formed by the first and second bridges 114a, 114b and vertices at the intersections 126. In some embodiments, the first and second bridges 114a, 114b are generally linear and thus form diamond-shaped cells. In some embodiments, the first and/or second bridges 114a, 114b can define a non-linear path such that the cells 118 outline shapes having at least one (e.g., two, three, four or more) curved sidewall and/or more or fewer than four sides.

At each of the intersections 126, the first and second bridges 114a, 114b may be configured to move relative to one another such that, as the device 100 elongates and compresses along its longitudinal axis L (FIG. 1B), the area of each of the cells 118 decreases and increases, respectively, and/or the shape of each of the cells 118 changes. As such, the first and second bridges 114a, 114b interact with one another along the bridge regions 104 similar to the interactions of braided filaments, thus imparting the mechanical properties of a braided mesh to the bridge regions 104. Thus, when the device 100 is implanted within a blood vessel along a tortuous curve, the bridge regions 104 better conform to the shape of the blood vessel, thus providing better wall apposition for the device 100 around the curve and avoiding the issues that often occur in other non-braided devices, such as tendencies to ovalize, kink, or fish mouth when placed in a body vessel with tortuous curvature. The braid-type architecture within the bridge regions 104 also aids in compressibility of the device 100, as well as loading and re-sheathability. In addition, the strut regions 102 of the device 100 provide the benefits of non-braided devices. For example, the fixed length of the strut regions 102 decrease the amount of foreshortening experienced when deploying the device 100, thus providing more stable and accurate deployment (as compared to other commercially available devices, including braided devices). Moreover, unlike braids that are formed of a plurality of braided wires, the expandable device 100 does not have loose wire ends and can be formed by thin film deposition (described in greater detail below), which allows the device 100 to have a much smaller wall thickness (e.g., less than or equal to 30 microns). The decreased profile of the device 100 results in faster endothelialization and healing. Accordingly, the device 100 of the present technology is a hybrid mesh design that incorporates the active/dynamic joints of a braided mesh with the stability and low profile potential of a non-braided mesh, resulting in a combination of mechanical properties that provides several advantages over conventional designs.

Figure 2B:
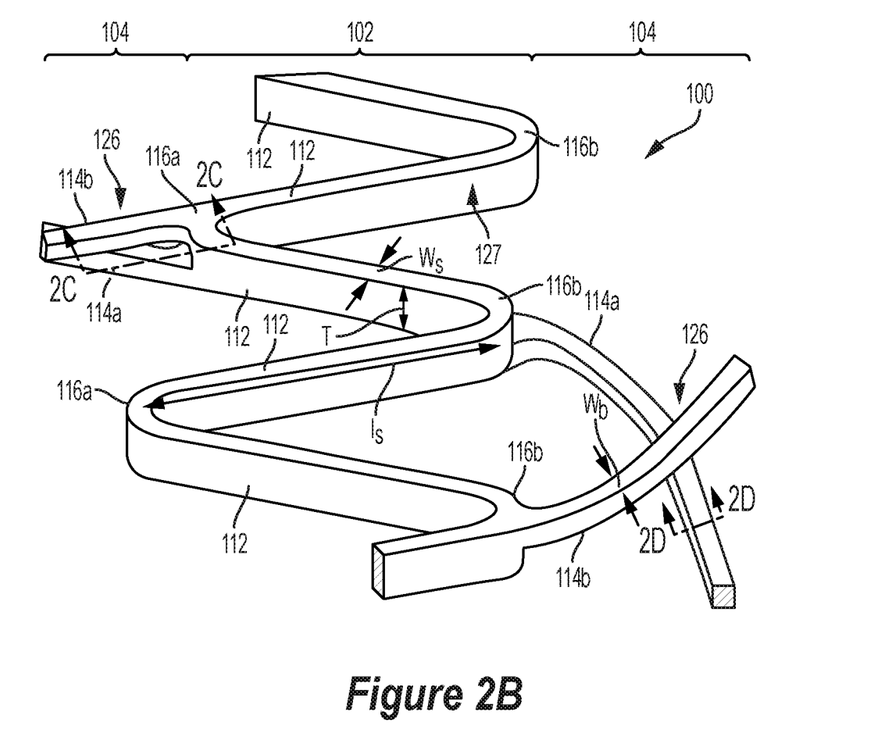
FIG. 2B is an enlarged, perspective view of a portion of the device as shown in FIG. 1A.
Figure 2C:
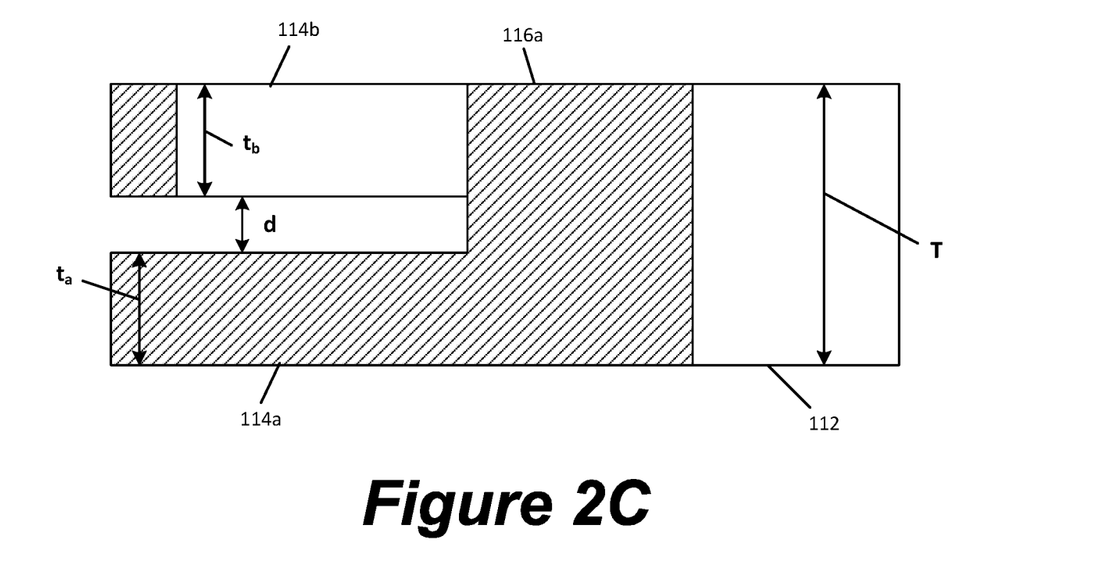
FIG. 2C is a cross-sectional view taken along line 2C-2C in FIG. 2B.
Figure 2D:
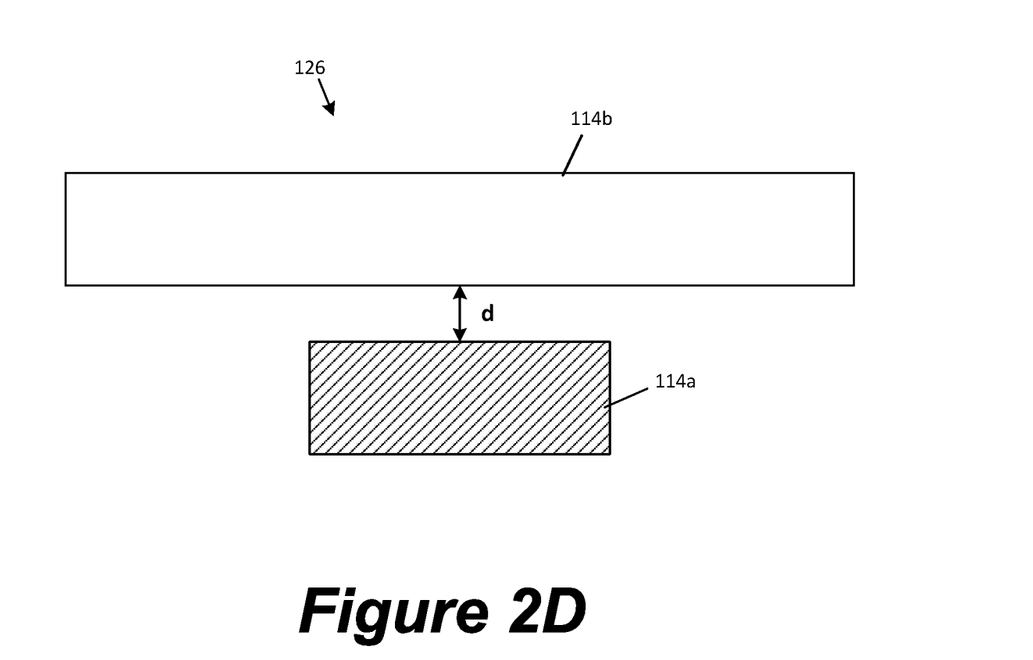
FIG. 2D is a cross-sectional view taken along line 2D-2D in FIG. 2B.

FIG. 2B is an enlarged view of a portion of one embodiment of the mesh 101 in the laid-flat configuration shown in FIGS. 1A and 2A, and FIGS. 2C and 2D are cross-sectional views taken along lines 2C-2C and 2D-2D, respectively. Referring to FIGS. 2B-2D together, the struts 112 have a strut thickness T and a strut edge surface 127 (FIG. 2B) extending along the strut thickness T. The respective thicknesses T of the struts 112, for example, can be measured along a line orthogonal to and extending radially from a central longitudinal axis of the expandable device 100. As shown in FIG. 2B, the bridges 112 may connect to and extend from the strut edge surfaces 127. In some embodiments, some or all of the bridges 112 may connect to and extend from the strut edge surfaces 127 at the apices 116. In some embodiments, the ends of the first bridges 114a may attach to the apices 116 at a first elevation and extend between adjacent strut regions 102 at that first elevation. The ends of the second bridges 114b may attach to the apices 116 at a second elevation different than the first elevation and extend between adjacent strut regions 102 at that second elevation. As used herein, "elevation" refers to a position relative to the central longitudinal axis of the device 100 measured along the radial dimension of the device 100 when in the tubular configuration. For example, as shown in FIGS. 2B-2D, the second bridges 114b may be radially further from the longitudinal axis of the device 100 than the first bridges 114a. In some embodiments, the second bridges 114b may be radially closer to the longitudinal axis of the device 100 than the first bridges 114a.

Referring to FIGS. 2C and 2D, a thickness $t_a$ of the first bridges 114a may be less than a thickness T of either of the connected struts 112, and a thickness $t_b$ of the second bridges 114b may be less than the thickness T of either of the connected struts 112. The thickness $t_a$ of the individual first bridges 114a may be less than, greater than, or equal to the thickness $t_b$ of the individual second bridges 114b. In some embodiments, the combined thickness of the first and second bridges (i.e., $t_a+t_b$) is less than the thickness T of either of the connected struts 112. In such embodiments, a top surface of the first bridges 114a may be separated from a bottom surface of the second bridges 114b by a (radial) distance d, as shown in FIGS. 2C and 2D. The distance d may be less than or greater than a thickness of either of the first or second bridges 114a or 114b. The distance d allows the first and second bridges 114a, 114b to move relative to one another at the intersections 126 without touching one another. In some embodiments, the distance d is negligible such that the first and second bridges 114a, 114b are in contact with one another but experience negligible friction such that they may slide past one another in response to compression or elongation of the mesh 101.

As used herein, "bridges 114" or "bridge 114" refers to any bridge embodiment disclosed herein, whether it be a first bridge 114a, a second bridge 114b, and/or a bridge that is not a first or second bridge 114a, 114b. In some embodiments, some or all of the bridge regions 104 include only first and second bridges 114a, 114b. In some embodiments, at least one of the bridge regions 104 includes at least the first and second bridges 114a, 114b, and at least another of the bridge regions 104 does not include the first bridges 114a, the second bridges 114b, or both. In some embodiments, the mesh 101 may have more than two bridges at different elevations and/or that intersect one another within the bridge regions 104. For example, in some embodiments the mesh 101 may have four bridges, each of which attaches at the apices at a different elevation and extends between adjacent strut regions 102 at different elevations. In some embodiments of the mesh 101, some of the bridge regions 104 do not include any intersecting bridges 114.

At least a portion of the first bridges 114a can be parallel to some or all of the other first bridges 114a of the same bridge region 104 and/or an adjacent bridge region 104 when the expandable device 100 is represented in a laid-flat view such as in FIGS. 1A and 2A. At least a portion of a first bridge 114a can have a helical shape and be parallel to some or all of the other first bridges 114a in a helical shape of the same bridge region 104 and/or an adjacent bridge region 104 when the expandable device 100 is considered in its tubular form. As used herein, two helical shapes are considered "parallel" if they wind about the same axis, at the same distance (i.e., radius) from the axis, with the same pitch angle or helix angle with respect to the axis, and in the same rotational direction (clockwise or counterclockwise) with respect to the axis. At least a portion of the second bridges 114b can be parallel to some or all of the other second bridges 114b of the same bridge region 104 and/or an adjacent bridge region 104 when the expandable device 100 is represented in a laid-flat view such as in FIGS. 1A and 2A. At least a portion of a second bridge 114b can have a helical shape and be parallel to some or all of the other second bridges 114b in a helical shape of the same bridge region 104 and/or an adjacent bridge region 104 when the expandable device 100 is considered in its tubular form.

An end of the first bridge 114a may be connected to the same or different apex 116 as an end of the second bridge 114b. In some embodiments of the device 100, for example as shown in FIG. 2A, at least some (including all) of the first apices 116a are connected to an end of a first bridge 114a and an end of a second bridge 114b (e.g., two bridges 114 extend from the first apex 116), and at least some (including all) of the second apices 116b are connected to either an end of a first bridge 114a or an end of a second bridge 114b (e.g., only one bridge 114 extends from a second apex 116). In some embodiments, all of the first apices 116a connected to a bridge 114 are connected to at least a first bridge 114a and a second bridge 114b. In some embodiments, each of a first bridge 114a and a second bridge 114b within the same bridge region 104 have an end that is connected to the same first apex 116a at a first side of the bridge region 104, and the corresponding opposite ends of the first and second bridges 114a, 114b are connected to different second apices 116b at the other side of the bridge region 104. Some or all of the strut regions 102 may have at least one free apex 116

(e.g., not directly connected to a bridge 114). In some embodiments, all of the apices 116 within some or all of the strut regions 102 are connected to a bridge 114 such that none of the apices 116 within the strut region 102 are free. According to some embodiments, some or all of the strut regions 102 may have a plurality of free first apices 116*a* and no free second apices 116*b* (e.g., all of the second apices 116*b* are connected to a bridge 114). In some embodiments, the first apices 116*a* within some or all of the strut regions 102 alternate in a circumferential direction along the strut region 102 between a free apex and a connected apex, and all of the second apices 116*b* are connected to either a first bridge 114*a* or a second bridge 114*b*. In such embodiments, each of the connected first apices 116*a* may be connected to a first bridge 114*a* and a second bridge 114*b*.

According to some embodiments, a helical winding direction of the first bridges 114*a* of one bridge region 104 can be different than a helical winding direction of the first bridges 114*a* of a different (e.g., adjacent) bridge region 104. For example, the helical winding direction of some first bridges 114*a* of one bridge region 104 can be clockwise and the helical winding direction of the first bridges 114*a* of a different bridge region 104 can be counterclockwise. The helical winding direction within any given bridge region 104 can be different than the helical winding direction of any adjacent bridge region 104. For example, alternating bridge regions 104 along a longitudinal length of the expandable device 100 can have first bridges 114*a* with alternating helical winding directions relative to each other. When the expandable device 100 is extended longitudinally, the first bridges 114*a* of the bridge regions 104 can straighten relative to the longitudinal axis. This allows the extreme ends of the expandable device 100 to rotate relative to each other less than they would if the first bridges 114*a* of every bridge region 104 were wound in the same helical direction, or not at all.

According to some embodiments, a helical winding direction of the second bridges 114*b* of one bridge region 104 can be different than a helical winding direction of the second bridges 114*b* of a different (e.g., adjacent) bridge region 104. For example, the helical winding direction of some second bridges 114*b* of one bridge region 104 can be clockwise and the helical winding direction of the second bridges 114*b* of a different bridge region 104 can be counterclockwise. The helical winding direction within any given bridge region 104 can be different than the helical winding direction of any adjacent bridge region 104. For example, alternating bridge regions 104 along a longitudinal length of the expandable device 100 can have second bridges 114*b* with alternating helical winding directions relative to each other. When the expandable device 100 is extended longitudinally, the second bridges 114*b* of the bridge regions 104 can straighten relative to the longitudinal axis. This allows the extreme ends of the expandable device 100 to rotate relative to each other less than they would if the second bridges 114*b* of every bridge region 104 were wound in the same helical direction, or not at all.

Referring to FIG. 2A, according to some embodiments, a bridge gap 122 is a distance between a pair of adjacent first bridges 114*a* or a pair of adjacent second bridges 114*b*. The bridge gap 122 can be measured across parallel portions of pairs of adjacent first bridges 114*a* or across parallel portions of pairs of adjacent second bridges 114*b*. The bridge gap 122 can be the same (e.g., uniform) or different among different pairs of first bridges 114*a* or amongst different pairs of second bridges 114*b* within a single bridge region 104. The bridge gap 122 can be the same/uniform or different for the first bridges 114*a* and/or the second bridges 114*b* among different bridge regions 104 of a single device 100. The bridge gap 122 can be 1 to 250 µm, for example greater than 100 µm.

According to some embodiments, each of the first bridges 114*a* and each of the second bridges 114*b* form a pitch angle 124 with respect to a line that is orthogonal to the longitudinal axis of the expandable device 100. A pitch angle 124 of one or more first bridges 114*a* within a bridge region 104 can be the same or different as the pitch angle 124 of one or more of the second bridges 114*b* within that bridge region 104. The pitch angle 124 can be the same/uniform or different amongst the first bridges 114*a* within a single bridge region 104. The pitch angle 124 can be the same/uniform or different amongst the second bridges 114*b* within a single bridge region 104. The pitch angle 124 of the first bridges 114*a* can be the same/uniform or different among different bridge regions 104 of a single device 100. The pitch angle 124 of the second bridges 114*b* can be the same/uniform or different among different bridge regions 104 of a single device 100. The pitch angle 124 can be 10 degrees to 60 degrees, for example 19 degrees.

Still referring to FIG. 2A, according to some embodiments, an apex gap 128 is a (circumferential) distance between a pair of adjacent apices 116 on a same longitudinal side of a strut region 102. When the device 100 is considered in a laid-flat form as shown in FIG. 2A, the apex gap 128 can be measured as orthogonal to a longitudinal axis of the expandable device 100. The apex gap 128 can be the same/uniform or different among different pairs of apices 116 within a single strut region 102. The apex gap 128 can be the same/uniform or different among different strut regions 102 of a single device 100. The apex gap 128 can be 10 to 450 µm, for example 300 µm.

According to some embodiments, a strut region length 130 is a longitudinal distance between opposing longitudinal sides of a strut region 102 (e.g., between a pair of bridge regions 104). The strut region length 130 can be measured as parallel to a longitudinal axis of the expandable device 100. The strut region length 130 can be the same/uniform or different among different strut regions 102 of a single device 100. The strut region length 130 can be 10 to 450 µm, for example 300 µm.

According to some embodiments, a bridge region length 132 is a longitudinal distance between opposing longitudinal sides of a bridge region 104 (e.g., between a pair of strut regions 102). The bridge region length 132 can be measured as parallel to a longitudinal axis of the expandable device 100. The bridge region length 132 can be the same/uniform or different among different bridge regions 104 of a single device 100. The bridge region length 132 can be 500 to 4500 µm, for example 1,100 µm.

According to some embodiments, some or all of the bridges 114 and/or some or all of the struts 112 can comprise a radiopaque marker. The radiopaque marker can be disposed on a substantially straight section of a bridge 114 and/or a strut 112, so the radiopaque marker is predominantly not subject to bending or flexing. For example, the radiopaque marker(s) can be disposed a distance away from an apex 116. The radiopaque marker(s) can be formed on the bridges 114 and/or the struts 112 by a process that is the same or different than a process used to form the bridges 114 and/or the struts 112, which are discussed further herein.

According to some embodiments, the expandable device 100 can provide a porosity that is the range of 5%-95%. The cells 118 of the expandable device 100 can provide a pore size that is between 5 and 450 µm. Generally, pore sizes described herein can be measured via a maximum inscribed circle technique.

A flow diverting cell size may be present in one, some or all of the bridge regions 104, or in the mesh 101 or device 100 as a whole. A "flow diverting cell size" can refer to an average cell size of cells 118 in the bridge region, mesh or device in question that is sufficiently small to inhibit flow of blood through the sidewall into an aneurysm to a degree sufficient to lead to thrombosis and healing of the aneurysm when the device 100 is positioned in a blood vessel and adjacent to or across the neck of the aneurysm. A device (or a device component, such as a mesh, sidewall or bridge region) that thus interferes with blood flow can be said to have a "flow diverting" property.

For example, a flow diverting cell size can be achieved at an average cell size of less than 500 microns when the device 100 is in the expanded state. (When "expanded state" is used herein to specify device parameters such as cell sizes, the expanded state is one that the device 100 can expand to (or be expanded to) within a straight, glass cylindrical tube with a constant inside diameter.) In some embodiments, a flow-diverting average cell size can be less than 320 microns, or in the range of 20-300 microns, or in the range of 25-250 microns, or in the range of 50-200 microns (inscribed diameter).

Instead of or in addition to a flow-diverting cell size, the device 100 (and/or a sidewall, mesh or bridge region thereof) can be provided with a porosity in the range of 5%-95% in the expanded state. In some embodiments, a porosity in the range of 30%-90% may be employed. Further, a porosity in the range of 50%-85% may be employed. Instead of or in addition to a flow-diverting cell size, the device 100 (and/or a sidewall, mesh or bridge region thereof) can be provided with a flow-diverting porosity.

Referring still to FIG. 2A, the strut 112 has a length $l_s$, a width $w_s$, and a thickness T, and the bridges 114 have length (not labeled in FIG. 2A), a width $w_b$, and a thickness (not labeled in FIG. 2A). The respective thicknesses of the struts 112 and the bridges 114 can be measured along a line orthogonal to and extending radially from a central longitudinal axis of the expandable device when the expandable device 100 is considered in a tubular shape or as a dimension that is orthogonal to a plane of the expandable device 100 when represented as laid-flat. The length $l_s$ of a strut 112 can be measured as a distance extending between ends of a strut 112, where the ends connect to another structure. The length $l_b$ of a bridge 114 can be measured as a distance extending between its ends along its central longitudinal axis. The respective widths of the struts 112 and the bridges 114 can be measured as the distance that is generally orthogonal to the length $l_s$ and thickness T. The width $w_s$ and length $l_s$ of a strut 112 can contribute to a surface coverage and porosity of the expandable device 100. According to some embodiments, the strut 112 can have a square cross-section. According to some embodiments, the bridge 114 can have a similar square cross-section. However, the strut 112 and/or the bridge 114 may have other suitable cross-sectional shapes, such as rectangular, polygonal, round, ovoid, elliptical, or combinations thereof.

According to some embodiments, a thickness of the struts 112 and/or the bridges 114 can be 5 to 50 µm, for example 50 µm. According to some embodiments, a width of the struts 112 and/or the bridges 114 can be 5 to 50 µm, for example 50 µm.

One or more of the first bridges 114a within a given bridge region 104 can have the same or different length, width, thickness, and/or pitch angle as one or more of the other first bridges 114a within the bridge region 104. In some embodiments, all of first bridges 114a of all of the bridge regions 104 can have the same length, width, thickness, and/or pitch angle. In some embodiments, all of first bridges 114a of one or more bridge regions 104 can have different length, width, thickness, and/or pitch angle as all of the first bridges 114a of some or all of the other bridge regions 104. One or more of the second bridges 114b within a given bridge region 104 can have the same or different length, width, thickness, and/or pitch angle as one or more of the other second bridges 114b within the bridge region 104. In some embodiments, all of second bridges 114b of all of the bridge regions 104 can have the same length, width, thickness, and/or pitch angle. In some embodiments, all of the second bridges 114b of one or more of the bridge regions 104 can have different length, width, thickness, and/or pitch angle as all of the second bridges 114b of some or all of the rest of the bridge regions 104.

Referring back to FIGS. 1A and 1B, the tapered regions 106 may extend circumferentially around the mesh 101 when the mesh 101 is in the tubular configuration. A proximal tapered region 106 may extend proximally from a proximal-most strut region 102, and a distal tapered region 106 may extend distally from the distal-most strut region 102. Each of the tapered regions 106 may include a plurality of tapered sub-regions 107 that include a plurality of struts. Within each sub-region 107, the plurality of struts may enclose a plurality of cells that increase in size (e.g., area) towards the ends of the mesh 101. One or both of the tapered regions 106 may be configured to detachably couple to a delivery member. In some embodiments, the mesh 101 does not include a tapered end region on one or both ends. In those embodiments with no tapered end regions, one or more of the strut regions and/or bridge regions may be configured to detachably couple to a delivery member.

The device 100 can be self-expanding, either by itself as a single tube, or by virtue of a second tubular member (not shown) disposed coaxially within the lumen of the device 100. The second tubular member can be a self-expanding braided, woven, laser-cut or deposited tube (or stent) and can be open at one or both ends. Alternatively, the device 100 can be expandable mainly or exclusively via a separate or removable mechanism such as a balloon.

Examples of Methods of Manufacture

The expandable device 100 may be formed, for example, by laser cutting a preformed tube or sheet, by interconnecting components (e.g., by laser welding), by vapor deposition techniques, or combinations thereof. The expandable device can be formed using known flexible materials such as nitinol, stainless steel, cobalt-chromium alloys, Elgiloy, magnesium alloys, tungsten, tantalum, platinum, or combinations thereof.

According to some embodiments, the expandable device 100 can be formed by a photolithography process. A substrate can be provided with a base for supporting the formation of the expandable device. The base (e.g., copper) can be used temporarily as a buffer between the substrate and a primary material used to form the expandable device. After the base is provided on the substrate, the primary material is provided thereon, for example by vapor deposition. The primary material can be provided as a thin film of substantially uniform thickness. Portions of the primary material can be removed to form the structure of the expandable device. For example, a photomask, based on a strut pattern, can be used to selectively expose portions of the primary material to light and etch the primary material into the desired shape for the expandable device. Alternatively or in combination, a chemical agent can be used to remove the portions of the primary material that are not protected by a photoresist. The base can then be eroded to separate the expandable device from the substrate. The expandable device can be further treated to form a desired shape (e.g., tubular) and have the desired heat set and/or shape memory properties.

In some embodiments, a first portion of the mesh 101 is formed during a first vapor deposition/patterning/etching sequence, and a second portion of the mesh 101 is formed during a second vapor deposition/patterning/etching sequence. For example, in some embodiments, the first bridges 114a are formed during a first vapor deposition/patterning/etching sequence, and the second bridges 114b are formed during a second vapor deposition/patterning/etching sequence. A sacrificial material can be deposited in those areas that (will eventually) underlie the second bridges 114b; once the second bridges 114b have been deposited atop the sacrificial material, the sacrificial material can be etched away or otherwise removed to leave the second bridges 114b overlying a vacant space in the completed mesh 101. In some embodiments, the struts 112 are formed by at least two vapor deposition/patterning/etching sequences.

According to some embodiments, the expandable device 100 can be formed by a laser cutting process. The expandable device may be formed by cutting a pattern of struts on a tube or on a flat sheet and then rolling the flat sheet into a generally tube-like or coiled shape. The expandable device in a generally tube-like or coiled shape can be circumferentially continuous or discontinuous. Where the expandable device is circumferentially discontinuous, portions of the expandable device can overlap in certain states.

Examples of Methods of Use

As mentioned elsewhere herein, the present disclosure includes methods of treating a vascular condition, such as an aneurysm, with any of the embodiments of the expandable devices (such as the device 100) disclosed herein. The expandable device could be deployed across the neck of an aneurysm and its flow-diverting properties employed to impede blood flow between the aneurysm and the parent vessel, cause the blood inside the aneurysm to thrombose, and lead to healing of the aneurysm. The expandable devices disclosed herein may also be used to treat other vascular defects. For example, the expandable devices of the present technology may be used to remove clot material from a blood vessel (e.g., as a thrombectomy device).

In order to implant any of the expandable devices disclosed herein, the expandable device can be mounted in a delivery system. Generally, the delivery system can comprise an elongate core member that supports or contains the expandable device, and both components can be slidably received in a lumen of a microcatheter or other elongate sheath for delivery to any region to which the distal opening of the microcatheter can be advanced. The core member is employed to advance the expandable device through the microcatheter and out the distal end of the microcatheter so that the expandable device is allowed to self-expand into place in the blood vessel, across an aneurysm or other treatment location. Accordingly, a vascular treatment apparatus can comprise a delivery system, such as any of the delivery systems described herein, and an expandable device, such as any of the expandable devices described herein, mounted in the delivery system.

A treatment procedure can begin with obtaining percutaneous access to the patient's arterial system, typically via a major blood vessel in a leg or arm. A guidewire can be placed through the percutaneous access point and advanced to the treatment location, which can be in an intracranial artery, or any neurovascular artery, peripheral artery or coronary artery. (As configured for neurovascular use, any of the expandable devices disclosed herein can have a diameter of 2-8 mm in the relaxed state or the expanded state; expandable devices used in the peripheral or coronary vasculature can have a diameter of 1-20 mm in the relaxed state or the expanded state.) The microcatheter is then advanced over the guidewire to the treatment location and situated so that a distal open end of the guidewire is adjacent to the treatment location. The guidewire can then be withdrawn from the microcatheter and the core member, together with the expandable device 100 mounted thereon or supported thereby, can be advanced through the microcatheter and out the distal end thereof. The expandable device 100 can then self-expand into apposition with the inner wall of the blood vessel. Where an aneurysm is being treated, the expandable device 100 is placed across the neck of the aneurysm so that a sidewall of the expandable device 100 (including the mesh 101) separates the interior of the aneurysm from the lumen of the parent artery.

According to some embodiments, when the expandable device 100 is bent to conform to a body vessel with tortuous curvature, the strut regions 102 can move closer to each other on the "inside-curving" side of the expandable device 100 when the bridges 114 collapse longitudinally and move closer to each other on that side. The thinness and arrangement of struts provides enhanced longitudinal flexibility and better arching capability. When deployed in a tortuous body vessel, the device of the subject technology will readily bend at a bridge region 104, thus providing improved wall apposition at a curve. For example, at an apex of a curve in the body vessel, the bridges 114 adjacent the apex move towards each other to facilitate contact with an inner surface of the vessel, thereby providing improved wall apposition near the apex. A distance between bridges 114 adjacent to the apex of the curve is less than a distance between bridges 114 disposed away from the apex. By allowing the bridge 114 to move near each other, the bridges 114 may better conform to the shape of the curve. As discussed above, this helps avoid issues that may occur in other devices, such as tendencies to ovalize, kink, or fish mouth when placed in a body vessel with tortuous curvature.

Once the expandable device has been placed, the core member and microcatheter are removed from the patient. The expandable device sidewall (e.g. the mesh 101) can now perform a flow-diverting function on the aneurysm, stagnating and/or thrombosing the blood in the aneurysm and leading to healing of the aneurysm.

Conclusion

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

It is understood that the specific order or hierarchy of steps in the processes disclosed is an illustration of exemplifying approaches. Based upon design preferences, it is understood that the specific order or hierarchy of steps in the processes may be rearranged. Some of the steps may be performed simultaneously. Various methods are disclosed presenting elements of the various steps in a sample order, and are not meant to be limited to the specific order or hierarchy presented.

Furthermore, to the extent that the term "include," "have," or the like is used herein, such term is intended to be inclusive in a manner similar to the term "comprise" as "comprise" is interpreted when employed as a transitional word in a claim.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The numbered clauses and their equivalents are intended to cover such forms or modifications as would fall within the scope and spirit of the subject technology.

I claim:

1. An expandable device comprising:
a plurality of strut regions extending circumferentially about the expandable device and including a plurality of struts, each of the struts having a strut thickness measured between a luminal surface and an abluminal surface of the respective strut; and
a plurality of bridge regions extending between adjacent strut regions and including a plurality of bridges, the plurality of bridges including first bridges and second bridges, each of the first bridges having a first bridge thickness measured between a luminal surface and an abluminal surface of the respective first bridge and each of the second bridges having a second bridge thickness measured between a luminal surface and an abluminal surface of the respective second bridge, wherein each of the first bridges intersects one or more of the second bridges within each of the bridge regions, and wherein the first bridges extend in a first rotational direction and the second bridges extend in a second rotational direction different than the first rotational direction,
wherein at least one of the first bridge thickness and the second bridge thickness is different than the strut thickness.

2. The expandable device of claim 1, wherein each of the struts is coupled to another strut at an apex, and wherein at least some of the apices connect to one of (a) one of the first bridges or (b) one of the second bridges.

3. The expandable device of claim 1, wherein each of the struts is coupled to another strut at an apex, and wherein at least one of the apices connects to one of the first bridges and to one of the second bridges.

4. The expandable device of claim 1, wherein the struts may be connected end-to-end within the strut regions such that the struts are circumferentially disposed in a zig-zag pattern.

5. The expandable device of claim 1, wherein the first bridge is spaced apart from the one or more second bridges at each intersection.

6. The expandable device of claim 1, wherein the expandable device is formed by thin-film deposition.

7. The expandable device of claim 1, wherein the expandable device is non-braided.

8. The expandable device of claim 1, wherein each of the first bridges intersects a plurality of second bridges within each of the bridge regions.

9. The expandable device of claim 1, wherein both the first bridge thickness and the second bridge thickness are less than the strut thickness.

10. The expandable device of claim 1, wherein the first bridges extend in a first rotational direction and the second bridges extend in a second rotational direction different than the first rotational direction.

11. An expandable device comprising:
a plurality of strut regions extending circumferentially about the expandable device and including a plurality of struts arranged end-to-end; and
a plurality of bridge regions extending between adjacent strut regions and including a plurality of bridges, the plurality of bridges including first bridges and second bridges that intersect one another within the bridge regions and together define a plurality of cells, wherein each of the cells enclose a cell area, and wherein the bridge regions are configured such that the cell areas decrease or increase in response to elongation or compression, respectively, of the expandable device along its longitudinal axis,
wherein each of the struts have a strut thickness measured between a luminal surface and an abluminal surface of the respective strut, each of the first bridges have a first bridge thickness measured between a luminal surface and an abluminal surface of the respective first bridge, and each of the second bridges have a second bridge thickness measured between a luminal surface and an abluminal surface of the respective second bridge, and wherein at least one of the first bridge thickness and the second bridge thickness is different than the strut thickness.

12. The expandable device of claim 11, wherein the expandable device is formed by thin-film deposition.

13. The expandable device of claim 11, wherein the first bridges are moveable relative to the second bridges at the intersections of the first and second bridges.

14. The expandable device of claim 11, wherein the expandable device is non-braided.

15. The expandable device of claim 11, wherein each strut has a strut edge surface extending along the strut thickness, and the bridges connect to and extend from the strut edge surfaces.

16. The expandable device of claim 11, wherein the first bridge thickness is less than the strut thickness.

17. The expandable device of claim 11, wherein the second bridge thickness is less than the strut thickness.

18. The expandable device of claim 11, wherein the combined first and second bridge thicknesses are less than or equal to the strut thickness.

19. An expandable device comprising:
a plurality of strut regions extending circumferentially about the expandable device and including a plurality of struts; and
a plurality of bridge regions extending between adjacent strut regions and including a plurality of bridges, the plurality of bridges including first bridges and second bridges,
wherein each of the struts have a strut thickness measured between a luminal surface and an abluminal surface of the respective strut, each of the first bridges have a first bridge thickness measured between a luminal surface and an abluminal surface of the respective first bridge, and each of the second bridges have a second bridge thickness measured between a luminal surface and an abluminal surface of the respective second bridge, and wherein at least one of the first bridge thickness and the second bridge thickness is less than the strut thickness, and
wherein the second bridges cross over the first bridges at intersections within the bridge regions, and wherein the first bridges are free to move relative to the second bridges at the intersections.

20. An expandable device comprising:
a plurality of strut regions extending circumferentially about the expandable device and including a plurality of struts, each of the struts having a strut thickness measured between a luminal surface and an abluminal surface of the respective strut; and
a plurality of bridge regions extending between adjacent strut regions and including a plurality of bridges, the plurality of bridges including first bridges and second bridges, each of the first bridges having a first bridge thickness measured between a luminal surface and an abluminal surface of the respective first bridge and each of the second bridges having a second bridge thickness measured between a luminal surface and an abluminal surface of the respective second bridge, wherein each of the first bridges intersects one or more of the second bridges within each of the bridge regions, and wherein the first bridge is spaced apart from the one or more second bridges at each intersection, and
wherein at least one of the first bridge thickness and the second bridge thickness is different than the strut thickness.

21. The expandable device of claim 20, wherein each of the struts is coupled to another strut at an apex, and wherein at least some of the apices connect to one of (a) one of the first bridges or (b) one of the second bridges.

22. The expandable device of claim 20, wherein each of the struts is coupled to another strut at an apex, and wherein at least one of the apices connects to one of the first bridges and to one of the second bridges.

23. The expandable device of claim 20, wherein the struts may be connected end-to-end within the strut regions such that the struts are circumferentially disposed in a zig-zag pattern.

24. The expandable device of claim 20, wherein the expandable device is formed by thin-film deposition.

25. The expandable device of claim 20, wherein the expandable device is non-braided.

26. The expandable device of claim 20, wherein each of the first bridges intersects a plurality of second bridges within each of the bridge regions.

27. The expandable device of claim 20, wherein both the first bridge thickness and the second bridge thickness are less than the strut thickness.

* * * * *

UNITED STATES PATENT AND TRADEMARK OFFICE
CERTIFICATE OF CORRECTION

PATENT NO. : 11,007,073 B2  
APPLICATION NO. : 16/413527  
DATED : May 18, 2021  
INVENTOR(S) : Animesh Choubey Page 1 of 1

It is certified that error appears in the above-identified patent and that said Letters Patent is hereby corrected as shown below:

On the Title Page

Item (57), Column 2, in "Abstract", Line 3, delete "b diverting" and insert -- by diverting --, therefor.

Item (57), Column 2, in "Abstract", Line 9, after "plurality" insert -- of --.

Signed and Sealed this  
Thirteenth Day of July, 2021

Drew Hirshfeld  
*Performing the Functions and Duties of the*  
*Under Secretary of Commerce for Intellectual Property and*  
*Director of the United States Patent and Trademark Office*